United States Patent [19]

McCabe et al.

[11] Patent Number: 5,288,296
[45] Date of Patent: Feb. 22, 1994

[54] PRODUCTION OF MICROBIAL FIELD CROP INOCULANTS

[75] Inventors: Dennis E. McCabe, Middleton; Brian J. Martinell, Madison; Alan Paau, Middleton; Lori L. Graham-Weiss, Madison, all of Wis.

[73] Assignee: W. R. Grace & Co., Columbia, Md.

[21] Appl. No.: 456,238

[22] Filed: Dec. 27, 1989

Related U.S. Application Data

[63] Continuation of Ser. No. 879,902, Jun. 30, 1986, abandoned, which is a continuation-in-part of Ser. No. 806,037, Dec. 6, 1985, abandoned.

[51] Int. Cl.$^5$ .............................................. A01N 63/00
[52] U.S. Cl. ...................................... 47/58; 435/822; 435/911; 424/93 R
[58] Field of Search ...................... 47/57.6, 58, 58.13, 47/58.26, 58.27, 57.604, 57.605; 435/252.1, 252.2, 253.6, 243, 254, 822, 911; 71/6, 7; 424/93 R, 93 C, 93 D, 93 Q

[56] References Cited

U.S. PATENT DOCUMENTS

| | | | |
|---|---|---|---|
| 2,098,918 | 11/1937 | Hendrickson | 435/252.2 |
| 2,726,948 | 12/1955 | Erickson | 71/7 |
| 2,932,128 | 4/1960 | Porter et al. | 47/58 |
| 2,995,867 | 8/1961 | Burton | 47/58 |
| 3,034,968 | 5/1962 | Johnston | 435/254 |
| 3,054,219 | 11/1962 | Porter et al. | 47/57.6 |
| 3,168,796 | 2/1965 | Scott et al. | 47/1.01 |
| 3,499,748 | 3/1970 | Fraser | 71/7 |
| 3,703,404 | 11/1972 | Kirk | 117/72 |
| 3,898,132 | 8/1975 | Hettrick | 435/260 |
| 4,149,869 | 4/1979 | Lloyd | 435/878 |
| 4,229,544 | 10/1980 | Haynes et al. | 435/252.1 |
| 4,259,317 | 3/1981 | Vesely et al. | 504/117 |
| 4,327,181 | 4/1982 | Litchfield et al. | 435/242 |
| 4,421,544 | 12/1983 | Jones et al. | 71/7 |
| 4,504,582 | 3/1985 | Swann | 435/108 |
| 4,512,103 | 4/1985 | Coulthard et al. | 47/1.1 |
| 4,550,527 | 11/1985 | Hall et al. | 47/58 |
| 4,551,165 | 11/1985 | Warner | 47/1.1 |

OTHER PUBLICATIONS

Biermann et al (1983) J. Amer. Hort. Sci. 108(6):972-976.
Rockel (1977) Aust. For. Res. 7:269-270.
Franco et al (1982) "Nodulation & Growth . . ." Plant and Soil 66: 149-60.
Marois, et al., "Biological Control of Verticillium Wilt of Eggplant in the Field," *Plant Disease*, vol. 66, No. 12, pp. 1166-1168 (1982).
Schroth, et al., "Disease-Suppressive Soil and Root-Colonizing Bacteria," *Science*, vol. 216, pp. 1376-1381 (1982).
Vincent, et al., "Death of Root-Nodule Bacteria on Drying," Manuscript, pp. 258-270 (1961).
Bitton, et al., "Influence of Clay Minerals, Humic Acid and Bacterial Capsular Polysaccharide on the Survival of *Klebsiella aerogenes* Exposed to Drying and Heating in Soils," *Plant and Soil*, vol. 45, 65-74 (1976).
Chao, et al., "Mineral Soils as Carriers for Rhizobium Inoculants," *Applied and Environmental Microbiology*, vol. 47, No. 1, Jan. 1984, pp. 94-97.
Dye, "A note on some factors affecting the survival of *Rhizobium* cultures during freeze drying and subsequent storage," *Journal of Applied Bacteriology*, vol. 52, pp. 461-464 (1982).

*Primary Examiner*—Che S. Chereskin
*Attorney, Agent, or Firm*—Quarles & Brady

[57] ABSTRACT

A method is disclosed for producing quantities of microbial inoculants for agricultural uses which involves preparing a medium of ground vermiculite, a nutrient and water. Wheat flour is disclosed as a preferred nutrient for fungal cultures. The medium is placed in containers, sterilized and inoculated with a microbial culture which grows out in the containers. The resulting product can be used moist or air-dried for ease in handling and storage. If the product is to be used moist, plastic bags may be used as the containers so that fermentation, formulation and packaging can all be handled in one step.

14 Claims, No Drawings

PRODUCTION OF MICROBIAL FIELD CROP INOCULANTS

This application is a continuation of U.S. Pat. application Ser. No. 06/879,902 filed Jun. 30, 1986 now abandoned which was a continuation-in-part of U.S. Pat. application Ser. No. 06/806,037 filed Dec. 6, 1985 now abandoned.

FIELD OF THE INVENTION

The present invention relates to methods for producing large quantities of stable and storable viable microbial materials in general, and relates, in particular, to methods for producing dried stable microbial formulations particularly advantageous for use as inoculants for agricultural field crops to improve their yield.

BACKGROUND OF THE INVENTION

It has long been known and practiced in agriculture that certain biological (i.e. microbial) inoculants can be used with certain selected crop species to facilitate the growth of crop plants of that species or to assist the crops of that species in resistance to particular pathogenic organisms. In addition, there is current research data suggesting that there may be several species of root-colonizing microorganisms which may be useful in promoting the growth of flowering plants or acting as antagonists to disease organisms, and thus acting to improve the yield of crop plants. Schroth and Hancock, "Disease-Suppressing Soil and Root-Colonizing Bacteria," *Science*, Vol. 216, pp. 1376–1381 (1982). The most long established use of microbial inoculants is the quite common practice of inoculating soybeans and other legumes at planting with bacterial cultures of the genus *Rhizobium*, so that the *Rhizobium* bacteria will form colonies in nodules within the roots of the soybean or other legume in which they will fix nitrogen symbiotically for the benefit of the plant as well as the bacteria. Currently this inoculation can be done by several techniques, none of which is optimal for all purposes. Techniques used in current practice include coating the seeds, dusting planted seeds or crops, or by spreading moist living inoculant in the furrows of planted seeds.

There has been a significant effort in the past to optimize products for preparing bacterial crop inoculants, focused particularly on *Rhizobium* inoculants. The typical process for preparing such inoculants usually requires both a fermentation process to grow up sufficient quantities of bacteria, and a stabilization or formulation process to either stabilize the mature bacteria for storage and shipment in an inactive state or to formulate the bacteria in an active culture for direct delivery to the field. Typically in the prior art the fermentation and formulation processes have been considered quite distinct, and one or more handling or processing operations are required to successfully transfer viable bacteria from fermentation to the formulation process. In addition, in prior art processes the usual carrier for viable *Rhizobium* cultures was peat. Since direct cultivation of bacteria on peat has not been commonly considered practical, because of microbial contaminants in peat, because peat is difficult to sterilize, and because toxic substances can be created in peat during sterilization, when a peat carrier has been used, a clear separation of the fermentation process from the formulation process was usually required.

It has also been recognized by some in the agricultural field that other, non-*Rhizobium* microbial organisms can foster the growth of common crop plants. For example, it has been known in the prior art that many fungi are found in association with the roots of certain specific vascular or woody plants. The type of association between fungi and plants is not well characterized and there is not a clear understanding or agreement among mycologists as to which of these associations are more properly characterized as symbiotic and which are more properly termed pathogenic. The association produced by a fungus with the roots of a plant is often referred to as a mycorrhizal association, although there is a poor understanding of this association.

It has now been reported specifically that some certain fungal species or strains have the capability to be antagonists for certain other plant pathogens. For example, it has been reported that the fungus *Talaromyces flavus* has the capability to be an antagonist for the fungal pathogen *Verticillium dahliae* in the cultivation of eggplant. Marois, et al., "Biological Control of Verticillium Wilt of Eggplant Solanum-Melongena in the Field", *Plant Disease*, 66:12, pages 1166–1168 (1982). Other fungal species have been reported to have similar effects. Papivizas, "Survival of Trichoderma-Harzianum in Soil and Pisum-Sativum Cultivar Perfectid-Freezer and Bean Phaseolus-Vulgaras Cultivar Blue-Lake", *Phytopathology*, 72:1, pages 122–125 (1982). In U.S. Pat. No. 4,259,317, a preparation for the protection of emerging sugar beets against damping-off, which is caused by a parasitic fungus, is disclosed which includes the use of the fungus *Pythium oligandrum*, which is used as an inoculant on the sugar beet seed to prevent damage to the plant by other fungal species.

One difficulty in using fungi as crop inoculants is the difficulty in propagating and producing large quantities of propagatable fungal material. The state of the art in fungal cultivation is not far advanced. For a fungal species to be useful as a crop inoculant, it must be producible in reasonable quantities and the end product of the production process must be reasonably easily handled and have a sufficiently long shelf life to be commercially useful. While it is possible for suitable microbial inoculants to be maintained in a living moist state, moist cultures present problems of transportation and storage. It is therefore obviously preferable if the fungi can be reduced to a dried or powdered state which is nevertheless viable upon planting in agricultural soils.

At least one prior attempt is known to devise a method for producing and preparing fungal agents for use as agricultural inoculants. That method is disclosed in U.S. Pat. No. 4,530,834 to Soper and McCabe, assigned to the United States Department of Agriculture. That method includes culturing the mycelia of a fungal agent in a suitable media and then harvesting the mycelia on a mesh screen to make mycelial mats. The mycelial mats are then treated with a protective agent, which is preferably a sugar solution, until they are saturated. The mycelia are then incubated and air dried at ambient room temperatures. The present invention is intended to be a more convenient methodology for creating a similar dried propogatable fungal product.

SUMMARY OF THE INVENTION

The present invention is summarized in that a method for producing microbial field crop inoculants includes the steps of: preparing a culture media including granular vermiculite, a quantity of a microbial nutrient, and water, into a flexible, disposable culture container; inoculating the culture media in the container with a culture of the microbial inoculant; and storing the container under conditions suitable for microbial growth so that the microbial culture grows out and matures on the media in the container.

It is an object of the present invention to provide a process for reliably producing quantities of stable microbial inoculants for crop plants.

It is another object of the present invention to provide such a process that is convenient and economical to implement, while still producing a superior product, because the process can combine the fermentation and formulation procedures in a single process.

It is an advantage of the present invention in that the process requires a minimum possible handling of the microbial culture.

Another advantage of the present process is that it makes possible the efficient fermentation and formulation of cultures of microbes for which no prior dependable protocols exist.

Other objects, advantages and features of the present invention will become apparent from the following specification.

In contrast to most prior art microbial fermentation procedures which primarily use liquid culture media, the process of the present invention envisions the use of a culture media including a particulate carrier dampened by a liquid (i.e. water) carrying a nutrient. The process introduces the carrier which will be ultimately distributed with the microbial product at the initiation of the fermentation process rather than growing the microorganisms on one media and then transferring them to a carrier. By introducing the carrier at this earlier stage, the present process reduces handling, measuring and transportation of the cultures so as to make the single-step fermentation and formulation process simple, economical and efficient.

DETAILED DESCRIPTION OF THE BEST MODE

The performance of the production process of the present invention thus begins with preparing a medium for microbial growth and formulation which includes a carrier. The medium includes a finely ground particulate carrier, preferably vermiculite, a nutrient selected for the organism, and water. The medium is put into containers and sterilized in the containers. The containers are preferably flexible, disposable receptacles such as simple polyethylene or polypropylene cups, buckets, trays or bags. The medium can then be inoculated with the microorganism, in the container, and the microbial culture grown out. After a growth period, the culture can then be used, as is, as a crop inoculant or can then be air dried, or stored in moist state for extended periods. The cultured organism, in the containers, can be stored in these same containers and then delivered for use. The product is stable, easy to use, and has high suitability for use in coating seeds uniformly.

The beginning step in the practice of the method of the present invention consists of preparing the culture medium. The bulk of the culture medium is made up of finely ground particulate or granular material which can serve as a microbial carrier. It has been found that vermiculite is the preferred material for the carrier, since it combines advantageous attributes of cost, availability, non-toxicity, uniformity, and workability. As will be seen from the process described, the vermiculite is not only used as the culture media, it is also used as the inoculant carrier. Vermiculite is suitable for both uses since it is naturally aerated and has an innate buffering capacity. Exfoliated vermiculite, in particular, offers the advantage of great surface area beneficial for microbial growth. Vermiculite is, of course, also inorganic and easy to sterilize. It has been found that finely ground vermiculite, ground to particulate size less than 40 mesh, usually 40-200 mesh, is suited for the practice of this invention. The most preferred size of vermiculite is between 45 and 80 mesh.

While vermiculite provides a substrate upon which microbial cultures may be grown, nutrients are also required for the growth of microbial inoculants. The appropriate nutrient should be selected for each microbial strain to be produced. For most rhizobial cultures it has been found that a nutrient composition of yeast extract and mannitol produces exemplary results. For other bacterial cultures, commercially available nutrient broths may be used successfully. For many fungal cultures and some bacterial cultures, quite surprisingly, it has been found that wheat and bran flour in general, and conventional white unbleached wheat flour in particular, has been found advantageous for use as a nutrient. It has discovered here that wheat flour seems, for reasons that are not fully understood, to be particularly advantageous with regard to the stability of the microbial product of many strains produced by this process. While other polysaccharides can be used, the resultant product, in particular for fungal products, is most stable when flour is used. In general, the amount of flour should be a small percentage of the amount of substrate material, in the range of 1.0 to 9% by dry weight. For fungal cultures or other cultures suitable for the flour nutrient it has been found that a dosage of unbleached white flour or bran flour at the rate of 1.3% dry weight of the weight of the vermiculite has been most suitable. For rhizobial cultures and other bacterial cultures, the optimal rate for the appropriate dry nutrient is 1.8% and 1.2% respectively.

The mixture must also then be moistened to provide suitable water for culture growth. The amount of water added to the granular substrate is also variable and subject to preference. It has been found that in general an amount of water equal to 60% of the granular substrate, again measured by weight, is most suitable for growth of the cultures. This ratio may also be expressed as 1.5 milliliter of water per gram of vermiculite. If a nutrient in solution is used, such as a yeast extract and mannitol solution, the nutrient solution can simply be added to the vermiculite in the 1.5 ml to 1 g ratio to add the appropriate amount of water to the culture as the nutrient is added.

It is envisioned in our version of the practice of the present invention that the medium thus formulated for microbial growth is introduced into a culture container, and preferably also sterilized, before the introduction of the microbial culture. This is done for reasons of convenience and ease of handling. If desired otherwise, it is perfectly possible to formulate the media in bulk, sterilize it, and then introduce it into previously sterilized containers in which the microbial culture is to be grown. It has been found that the process works most expeditiously, however, when the containers for the cultures are simple, flexible, plastic resin receptacles, such as ordinary polypropylene film bags. The mixture can be introduced into the receptacles in appropriate quantities, and the culture containers with the media therein can then be autoclaved to create sterilized media and sterilized receptacles in one step. After sterilization, the media and the receptacle are then cooled before use.

The sterilized receptacles containing the appropriate mixture of media therein are then inoculated with the culture of the culture to be grown. For bacteria, the inoculation should consist of a culture of the bacteria. For fungi, the inoculation should consist of spores or other propagatable material. After the introduction of the microbial culture, the receptacle should be closed. Polypropylene bags can easily be closed by means of heat seals which deform the bags to make sealed containers or they can also be easily mechanically closed with fasteners or other similar devices. The receptacles are then stored under conditions which are suitable for growth of the microbial culture. Usually the receptacles can simply be left at room temperature for time periods sufficient for the culture to grow out on the media provided in the receptacle. It has been found that for most fungi, a time period in excess of thirty, and preferably at least forty-five, days is necessary for optimal growth and stability of the cultures grown at room temperatures. For bacteria, a time period in excess of 7, and preferably at least 30 days is satisfactory.

Once the microbial culture is cultivated in the receptacles, the material can either be used as an agricultural inoculant, as is, straight from the receptacle, or the material can be removed from the receptacle and dried for use as a dry inoculant or as a seed coating. If the material is to be used moist from the receptacle, then the receptacle itself, preferably a plastic bag, can be used as the storage and shipment container. The microorganisms, particularly bacteria, will reach a limit of population density in the receptacle and then become dormant. The moist microbial mixture, carried on the vermiculite, can be used directly from the bags, either by separate introduction into the furrow or by mixing with seeds at time of planting. For many cultures, and in particular fungal cultures, however, dried material offers attractive benefits of ease of handling and stability.

If the fungal culture is to be dried, the cultivation period in the receptacle must be selected. In general, for time periods much less than thirty days, the shelf life and stability of a dried inoculant is adversely affected. As cultures mature for a time period in excess of thirty days before drying, the dried product becomes increasingly stable and exhibit increased viability even after long periods of shelf storage. It has been found that the stability of dried cultures generally does not increase dramatically after cultures have been grown out forty-five days, and accordingly for most efficient production processing of dried inoculant, a forty-five day time period of culture grow-out is preferred. After the culture has grown out inside of the receptacle for the requisite grow-out time period, the receptacle is simply opened and the culture is air-dried at room temperatures. The culture is left, exposed to the open air at normal room temperature in rooms suitable for human habitation, for time periods sufficient until the moisture level in the culture equilibriates with the relative humidity in the room in which the cultures have been dried.

It has been found that dried microbial cultures of fungi produced by this method are stable and can be easily handled. The cultures appear granular in character and can be easily used for agricultural purposes, either by spreading in the fields or by coating onto seeds. The dried cultures thus produced are viable for a time period exceeding at least two months with little, if any, degradation of the viability of the fungi during that time period. In addition, the present production process is efficient to utilize and economical in its operation. Since the same containers are used for sterilization and propagation of the microbes, handling of the various components of the process and handling of the microbial cultures themselves is minimized. Since the process does not require specialized containers or receptacles, the materials necessary for performing the process are economically attractive and easily obtainable. Accordingly, the process offers one which is efficient and economical while still offering a product having high stability, uniformity, while retaining optimal viability.

Example 1

A granular substrate of 20 grams of 40 mesh vermiculite was mixed with 0.26 grams of wheat flour and 13 milliliters of water. The mixture was mixed together in a container and placed in 4 ounce polypropylene specimen cups.

The specimen cups were sealed and then sterilized by autoclaving. The cups were then allowed to cool.

Once the cups were cooled, the cups were re-opened and inoculated with propagules of *Marasmius creates*, a species of fungus. The cups were resealed to be airtight. The cups were then left at room temperature in a laboratory for forty-five days.

After forty-five days, the cups were opened and the cultures were air dried in open trays for two days.

The dried culture thus produced was assayed for stability and viability of the cultures. It was found that the dried culture produced contained at least 106 viable propagules of *M. oreates* per gram. After six weeks of shelf storage, the viability test was repeated with no significant degradation in the measurable viability of the dried culture.

Example 2

Cultures of each of the fungi listed in Table 1 below were inoculated into one-half gallon autoclaved plastic jars into each of which had been previously placed 500 grams of a vermiculite, flour and water growth medium prepared in proportions as in Example 1 above. Approximately 0.5 gram of inoculum of fungal culture was added to each jar, after which the media was mixed thoroughly.

Measurements of the activity level of the fungi in the media, measured again in propagules per gram, were made 2–4 weeks after inoculation. The jars were stored at room temperature throughout. Additional measurements of activity were made six months after inoculation.

Each fungal culture is identified in the Table to the full extent known to the investigators.

TABLE 1

| Fungal Culture | | Initial Activity Level (Calculated) | Mature Activity Level (2–4 weeks) | Storage Activity Level (6 months) |
|---|---|---|---|---|
| 144 | (*Marasmius oreates*) | $9 \times 10^3$ | $9 \times 10^6$ | $2 \times 10^6$ |
| 189 | (Trichoderma) | $1 \times 10^4$ | $1 \times 10^7$ | $3 \times 10^7$ |
| 191 | (Mortierella) | $8 \times 10^2$ | $8 \times 10^5$ | $6 \times 10^5$ |
| 231 | (Mucor) | $1 \times 10^2$ | $1 \times 10^5$ | $4 \times 10^5$ |
| 238 | (Mucorales) | $2 \times 10^3$ | $2 \times 10^6$ | $4 \times 10^6$ |
| 257 | (Trichoderma) | $2 \times 10^4$ | $2 \times 10^7$ | $3 \times 10^7$ |
| 258 | (Trichoderma) | $2 \times 10^5$ | $2 \times 10^8$ | $3 \times 10^8$ |
| 274 | (Trichoderma) | $2 \times 10^5$ | $2 \times 10^8$ | $2 \times 10^8$ |
| 284 | (Ascomycetes) | $3 \times 10^3$ | $3 \times 10^6$ | $8 \times 10^5$ |

TABLE 1-continued

| Fungal Culture | | Initial Activity Level (Calculated) | Mature Activity Level (2–4 weeks) | Storage Activity Level (6 months) |
| --- | --- | --- | --- | --- |
| 285 | (Phoma) | $1 \times 10^3$ | $1 \times 10^6$ | $2 \times 10^6$ |
| 301 | (Mucor) | $1 \times 10^3$ | $1 \times 10^6$ | $4 \times 10^6$ |
| 303 | (Trichoderma) | $6 \times 10^3$ | $6 \times 10^6$ | $3 \times 10^7$ |
| 331 | (Alternaria) | $8 \times 10^2$ | $8 \times 10^5$ | $6 \times 10^5$ |
| 332 | (Trichoderma) | $1 \times 10^4$ | $1 \times 10^7$ | $2 \times 10^7$ |
| 490 | (Ascomycetes) | $4 \times 10^3$ | $4 \times 10^6$ | $5 \times 10^7$ |
| 491 | (Ascomycetes) | $3 \times 10^3$ | $3 \times 10^6$ | $1 \times 10^7$ |
| 545 | (Rhizopus) | $1 \times 10^2$ | $1 \times 10^5$ | $3 \times 10^5$ |
| 546 | (Mortierella) | $8 \times 10^2$ | $8 \times 10^5$ | $9 \times 10^5$ |
| 744 | (Cylindrocarpon destructans) | $8 \times 10^4$ | $8 \times 10^7$ | $6 \times 10^6$ |

Example 3

Cultures of each of the fungi listed in example 2 above were again prepared using the identical process. The cultures produced were then air dried. A measurement of the level of activity, again using standard dilution techniques, was made upon drying. The dried culture was then stored at room temperature for six weeks after which culture viability was again measured. The results are summarized in Table 2 below.

TABLE 2

| Fungal Culture | | Activity Level at Production | Activity Level After Six Weeks |
| --- | --- | --- | --- |
| 144 | Marasmius oreates | $3 \times 10^5$ | $2 \times 10^3$ |
| 189 | Trichoderma | $3 \times 10^6$ | $2 \times 10^6$ |
| 191 | Mortierella | $2 \times 10^5$ | $7 \times 10^4$ |
| 231 | Mucor | $2 \times 10^5$ | $1 \times 10^5$ |
| 238 | Mucorales (order) | $1 \times 10^6$ | $2 \times 10^6$ |
| 257 | Trichoderma | $2 \times 10^6$ | $2 \times 10^6$ |
| 258 | Trichoderma | $1 \times 10^8$ | $1 \times 10^8$ |
| 274 | Trichoderma | $8 \times 10^7$ | $1 \times 10^8$ |
| 284 | Ascomycetes (Class) | $2 \times 10^5$ | $9 \times 10^4$ |
| 285 | Phoma | $4 \times 10^5$ | $2 \times 10^5$ |
| 301 | Mucor | $2 \times 10^5$ | $1 \times 10^6$ |
| 303 | Trichoderma | $3 \times 10^6$ | $1 \times 10^7$ |
| 331 | Alternaria | $6 \times 10^5$ | $5 \times 10^5$ |
| 332 | Trichoderma | $3 \times 10^7$ | $2 \times 10^7$ |
| 474 | Alternaria | $5 \times 10^5$ | $6 \times 10^4$ |
| 475 | Cladosporium | $2 \times 10^7$ | $9 \times 10^6$ |
| 490 | Ascomycetes (Class) | $1 \times 10^7$ | $3 \times 10^6$ |
| 491 | Ascomycetes (Class) | $6 \times 10^6$ | $2 \times 10^6$ |
| 545 | Rhizopus | $2 \times 10^4$ | $6 \times 10^4$ |
| 546 | Mortierella | $2 \times 10^5$ | $6 \times 10^4$ |
| 744 | Cylindrocarpon destructans | $2 \times 10^6$ | $3 \times 10^6$ |

Example 4

A portion of the dried formulation of each culture prepared in Example 3 above was also segregated for cold storage viability testing. Samples of each of the dried cultures wee refrigerated for five months at 4° C. The activity level in each culture was measured after three and five months of storage. The results are listed in Table 3 below.

TABLE 3

| Fungal Culture | | Activity Level at Production | Activity Level After 3 Months | Activity Level After 5 Months |
| --- | --- | --- | --- | --- |
| 144 | (Marasmius oreates) | $3 \times 10^5$ | $3 \times 10^5$ | $1 \times 10^5$ |
| 189 | (Trichoderma) | $3 \times 10^6$ | $1 \times 10^7$ | $9 \times 10^6$ |
| 191 | (Mortierella) | $2 \times 10^5$ | $5 \times 10^4$ | $4 \times 10^5$ |
| 231 | (Mucor) | $2 \times 10^5$ | $3 \times 10^5$ | $9 \times 10^5$ |
| 238 | (Mucorales) | $1 \times 10^6$ | $2 \times 10^6$ | $8 \times 10^6$ |
| 257 | (Trichoderma) | $2 \times 10^6$ | $5 \times 10^6$ | $2 \times 10^7$ |
| 258 | (Trichoderma) | $1 \times 10^8$ | $2 \times 10^8$ | $7 \times 10^7$ |
| 274 | (Trichoderma) | $8 \times 10^7$ | $5 \times 10^7$ | $5 \times 10^7$ |
| 284 | (Ascomycetes) | $2 \times 10^5$ | $4 \times 10^5$ | $3 \times 10^5$ |
| 285 | (Phoma) | $4 \times 10^5$ | $5 \times 10^5$ | $2 \times 10^6$ |
| 301 | (Mucor) | $2 \times 10^5$ | $2 \times 10^6$ | $7 \times 10^6$ |
| 303 | (Trichoderma) | $3 \times 10^6$ | $2 \times 10^7$ | $2 \times 10^7$ |
| 331 | (Alternaria) | $6 \times 10^5$ | $1 \times 10^6$ | $2 \times 10^6$ |
| 332 | (Trichoderma) | $3 \times 10^7$ | $4 \times 10^7$ | $4 \times 10^7$ |
| 474 | (Alternaria) | $5 \times 10^5$ | $6 \times 10^5$ | $1 \times 10^6$ |
| 475 | (Cladosporium) | $2 \times 10^7$ | $1 \times 10^7$ | $9 \times 10^6$ |
| 490 | (Ascomycetes) | $1 \times 10^7$ | $1 \times 10^7$ | $1 \times 10^7$ |
| 491 | (Ascomycetes) | $6 \times 10^6$ | $1 \times 10^7$ | $1 \times 10^7$ |
| 545 | (Rhizopus) | $2 \times 10^4$ | $8 \times 10^4$ | $2 \times 10^6$ |
| 546 | (Mortierella) | $2 \times 10^5$ | $3 \times 10^5$ | $6 \times 10^5$ |
| 744 | (Cylindrocarpon destructans) | $2 \times 10^6$ | $9 \times 10^6$ | $5 \times 10^6$ |

Example 5

Standard commercially available vermiculite was ground in a Wiley mill to nominally 40 mesh. The ground vermiculite was sieved to yield a 45–80 mesh fraction which was bagged in flexible polypropylene bags which were used as the culture receptacles. The vermiculite, in the bags, was autoclaved for 45 minutes.

A culture of *Rhizobium japonicum* isolated from a soybean field in Iowa was grown to a stationary phase in a yeast extract-mannitol broth. The stationary phase condition of this starter culture was determined by optical density measurements which remained constant when stationary phase was reached. A sample was drawn from the starter culture and diluted with fresh yeast extract-mannitol broth such that the bacterial density in the bacteria-nutrient solution was slightly less than $10^4$ bacteria per milliliter of liquid. The bacterial-nutrient solution was then added to the vermiculite in the bags at a ratio of 1.5 milliliter solution per gram of vermiculite. The liquid and vermiculite were then mixed thoroughly and the bags sealed. The bags were then stored at room temperature for bacteria growth. The following table summaries the grow-out of sample cultures.

TABLE 4

| | Bacterial Density (per g.) | | |
| --- | --- | --- | --- |
| Sample No. | Initial (t = o) | Seven Days | Thirty Days |
| 1 | $1.4 \times 10^4$ | $1.7 \times 10^8$ | $1.3 \times 10^9$ |
| 2 | $1.4 \times 10^4$ | $3.1 \times 10^8$ | $1.3 \times 10^9$ |
| 3 | $1.4 \times 10^4$ | $3.2 \times 10^8$ | $1.6 \times 10^9$ |
| 4 | $1.4 \times 10^4$ | $3.2 \times 10^8$ | $1.0 \times 10^9$ |

Thus a grow-out of approximately 100,000 times was obtained in thirty days. The resulting densely populated bacterial culture was granular and at an appropriate density suitable for direct field application. Since it is usual in the industry to coat seeds with inoculant at a density of $10^8$ bacteria per gram to obtain $10^5$ bacteria per seed, the density achieved here even allows for a one log loss of viability will still achieve sufficient bacterial density for use. Thus the *Rhizobium* culture in the bag was suitable for field use without further treatment because it already contained a suitable carrier and a dense viable culture.

Example 6

To demonstrate the utility of this method for other *Rhizobium* strains, the regimen was repeated for four other strains of *Rhizobium japonicum*, three mutants of a wild-type bacteria isolated from a soybean plant in Louisiana and one culture isolated from a soybean plant in Minnesota. The cultivation procedure was the same, and the log growth curve achieved formed a similar pattern as in Example 5 above, as summarized below.

TABLE 5

| Isolate No. | Bacterial Density (bacteria/gram) | |
|---|---|---|
| | Initial | After 7 Days |
| Mutant 1 | $3.6 \times 10^5$ | $8.0 \times 10^8$ |
| Mutant 2 | $3.9 \times 10^5$ | $1.5 \times 10^9$ |
| Mutant 3 | $1.9 \times 10^6$ | $6.0 \times 10^8$ |
| Minnesota Strain | $5.1 \times 10^4$ | $6.9 \times 10^8$ |

These results confirm that the procedure is not strain dependent.

Example 7

To further verify that the procedure is suitable for use with a wide variety of non-Rhizobium bacteria, the regimen of Example 5 was repeated with six specimens of soil bacteria. The six specimen cultures were soybean root-associated cultures which do not modulate soybean roots and differ in both growth rate and cell and colony morphology from *Rhizobium*. The cultures have not been taxonomically classified. The cultures were similarly treated, as the *Rhizobium*, except that a common commercially available nutrient broth was used instead of the yeast extract-mannitol broth, and the results are summarized as follows:

TABLE 6

| Isolate | Bacterial Density (bacterial/gram) | |
|---|---|---|
| | Initial | After 12 Days |
| No. 1 | $8.0 \times 10^4$ | $3.0 \times 10^8$ |
| No. 2 | $8.0 \times 10^4$ | $5.1 \times 10^9$ |
| No. 3 | $8.0 \times 10^4$ | $2.7 \times 10^9$ |
| No. 4 | $8.0 \times 10^4$ | $2.5 \times 10^9$ |
| No. 5 | $8.0 \times 10^4$ | $1.1 \times 10^{10}$ |
| No. 6 | $8.0 \times 10^4$ | $9.6 \times 10^8$ |

These results demonstrate that the procedure is suitable for a wide variety of soil dwelling or root-associate bacteria of possible agricultural interest. While the log growth curves may vary from species to species, significant high growth rates were obtained for these cultures. Because of the efficiencies offered by the present process, its use for most known or unknown soil associated microorganism is possible.

We claim:

1. A method for producing microbial field crop inoculant in a culture container whereby the inoculants are fermented and stored until use in the same culture container, consisting essentially of the steps of:

introducing a culture medium, including finely ground vermiculite, a sufficient quantity of a nutrient appropriate for growth of the inoculant, and water in an amount as needed to moisten the vermiculite, into a culture container, the vermiculite in the container serving as an inoculant growth substrate and a particulate carrier;

inoculating the culture medium in the container with a starter culture of a microbial inoculant selected from the group consisting of bacterial and fungal inoculants;

closing the container;

storing the closed container at a temperature suitable for microbial growth, substantially free from agitation or aeration, so that the microbial culture first grows out and then matures on the medium in the container; and delivering the inoculant for sue on the same carrier and in the same container in which it was grown.

2. A method as claimed in claim 1 wherein the nutrient is flour.

3. A method as claimed in claim 2 wherein the flour is unbleached white wheat flour.

4. A method as claimed in claim 2 wherein the ratio by dry weight of flour to vermiculite is between 1.3 and 9 percent.

5. A method as claimed in claim 4 wherein the ratio of dry weight of flour to vermiculite is approximately 1.3 percent.

6. A method as claimed in claim 4 wherein the ratio by weight of water to vermiculite is about 60 percent.

7. A method as claimed in claim 1 wherein the vermiculite is ground to a size generally smaller than 40 mesh.

8. A method as claimed in claim 1 further comprising the step, before the inoculating step, of sterilizing the culture container with the medium therein.

9. A method as claimed in claim 7 wherein the serialization is performed by autoclaving.

10. A method as claimed in claim 1 wherein the microbial inoculant is a fungus.

11. A method as claimed in claim 1 wherein the microbial inoculant is a bacterium.

12. A method as claimed in claim 11 wherein the bacteria is a strain of *Rhizobium*.

13. A method as claimed in claim 1 wherein the culture container is a plastic bag.

14. A method for preparing a fungal or bacterial field crop inoculant consisting essentially of the steps of:

preparing in a sealable plastic bag a quantity of sterilized culture medium comprising vermiculite carrier, nutrient, and an amount of water limited to a quantity sufficient to moisten the vermiculite;

inoculating a culture medium with the fungal or bacterial culture;

sealing the bag to the air;

storing the bag at room temperature so as to allow the microbial culture to grow out in the medium in the bag substantially free from agitation or aeration; and delivering the inoculants for use in the bag.

* * * * *